United States Patent [19]

Nadai et al.

[11] Patent Number: 4,889,528

[45] Date of Patent: Dec. 26, 1989

[54] DRIP INFUSION RATE CONTROL APPARATUS

[75] Inventors: Tanekazu Nadai, 4-26 Minami Shinchi, Fushimi-ku, Kyoto; Toshio Kawara, Uji, both of Japan

[73] Assignees: Shimadzu Corporation; Tanekazu Nadai, Osaka, Japan

[21] Appl. No.: 162,059

[22] Filed: Feb. 29, 1988

[30] Foreign Application Priority Data

Feb. 27, 1987 [JP] Japan .................................. 62-046217
Aug. 3, 1987 [JP] Japan .................................. 62-193996
Aug. 28, 1987 [JP] Japan .................................. 62-215918
Aug. 28, 1987 [JP] Japan .................................. 62-215919

[51] Int. Cl.$^4$ ............................................ A61M 31/00
[52] U.S. Cl. ...................................................... 604/65
[58] Field of Search ................................... 604/50, 65

[56] References Cited

U.S. PATENT DOCUMENTS 4,457,750 7/1984 Hill ........................................ 604/65
4,467,844 8/1984 DiGianfilippo et al. ......... 604/65 X
4,600,401 7/1986 Kamen .................................. 604/65
4,670,007 6/1987 Wheeldon et al. .................... 604/65

*Primary Examiner*—John D. Yasko
*Attorney, Agent, or Firm*—Koda & Androlia

[57] ABSTRACT

A drip infusion rate control apparatus controlling the flow rate of a medical solution to be infused into a human or animal body by means of a drip infusion system. The apparatus includes a weight measuring means for measuring the weight of a medicine bottle containing a medical solution being infused into a human or animal body through an infusion tube led out from the medicine bottle, an existing flow rate data computing means for computing, by using at least time-dependently varying weight data outputted from the weight measuring means, an existing flow rate reflecting value which reflects an existing flow rate of the medical solution flowing in the infusion tube, an aiming value outputting means for outputting a set of reference flow rate data defining an aiming flow rate expected to the medical solution, a basic data inputting means for inputting a set of basic data necessary for the aiming value outputting means to output the set of reference flow rate data, a comparator for comparing the existing flow rate reflecting value with at least one of the reference flow rate data contained in the set of reference flow data, and outputting a flow rate control signal, and a flow rate regulating mechanism interposed midway of the infusion tube, the mechanism being operative according to the flow rate control signal outputted from the comparator.

8 Claims, 7 Drawing Sheets

FIG.7(A)
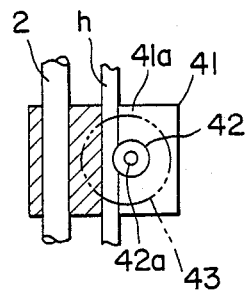
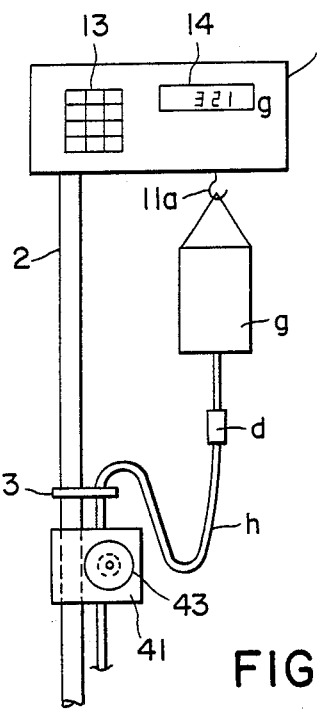
FIG.6
FIG.7(B)
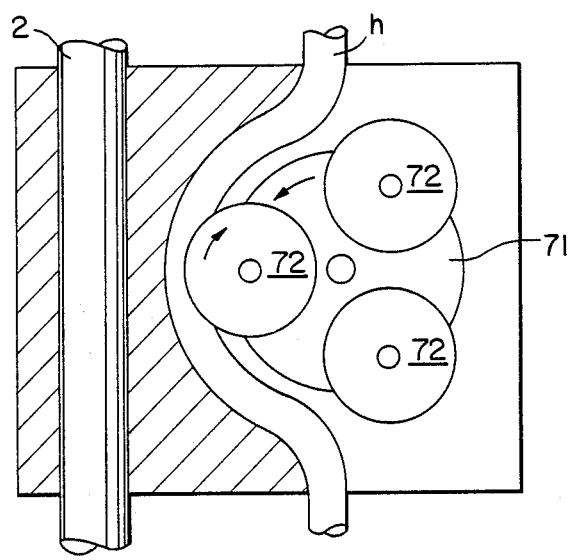

DRIP INFUSION RATE CONTROL APPARATUS

BACKGROUND OF THE INVENTION

The present invention relates to an apparatus to automatically control the infusion rate or speed of a drip infusion system.

As a method of injecting a medical solution into a living body, a drip infusion system is well known, in which a medical solution contained in a medicine bottle in gravitationally infused into an object through an infusion tube provided at one end with an infusion needle, the tube connecting between the the bottle and the object with the needle thrusted into the body. Midway of the infusion tube there are provided in series a transparent drip chamber and a flow rate regulation clamp. The flow rate of the medical solution being infused is manually controlled with the clamp adjusted depending on intuition and experience in accordance with the size and frequency of droplets seen falling in the drip chamber. In spite of the fact that the speed of infusion is possibly an important factor in medical treatment, it is difficult or troublesome to obtain an optimum infusion condition by means of such a manual flow rate control made depending on intuition and experience. Further, it is inconvenient that the clamping is necessarily readjusted for a temperature variation, because the infusion speed depends on temperature through the temperature dependence of the viscosity and surface tension of the medical solution.

OBJECTS AND SUMMARY OF THE INVENTION

The present invention aims at improving the above mentioned inconveniences and disadvantages accompanying a simple drip infusion system, and makes it an object to provide a drip infusion rate apparatus, which automatically controls the flow rate of the medical solution being infused into a living body by a drip infusion system.

Another object of the invention is to add to such an control apparatus a function of temporarily stopping the control operation for the purpose of complying, for instance, with a condition in which a proper control operation is made impossible because of the medicine bottle and infusion tube violently rolling and swinging owing to transferring the infusion system together with an patient receiving the infusion.

A further object of the invention is to further add to the control apparatus a function of stopping the infusion operation with an alarm raised when an infusion rate deviates from a predetermined allowable range for some reason or other.

To achieve the above objects, the drip infusion rate control apparatus based on the present invention comprises the following six fundamental constituents; a weight measuring means for weighing the medicine bottle in a drip infusion system to which the present invention is applied; an existing flow rate data computing means for computing an existing flow rate reflecting value from the time-dependently varying weight data outputted from said weight measuring value; an aiming means outputting means for outputting a set of reference flow rate data which define an aiming flow rate expected to a medical solution being infused by the above drip infusion system; a basic data inputting means for inputting a set of basic data necessary for said aiming value outputting means to output said set of reference rate data; a comparator for comparing, to output a flow rate control signal, said existing flowrate reflecting value with an aiming flow rate defined by said set of reference flow rate data outputted from said aiming value outputting means; and a flow rate regulating mechanism interposed midway of the infusion tube in the above drip infusion system and being operative in accordance with said flow rate control signal outputted from said comparator. As is understood from the above briefed fundamental consitution, the apparatus based on the present invention controls the speed of infusion so as to keep it at an aiming flow rate by comparing an existing flow rate with an aiming flow rate expected to the medical solution being infused. The drip infusion rate control apparatus briefed above can further be accompanied by an control operation stopping function capable of being put into action by a manual switching operation and/or an infusion stopping function of alarming and stopping the infusion operation in an emergency.

According to the present invention, not only the infusion speed is automatically kept at an aiming flow rate, but also the infusion rate control can be temporarily stopped to avoid an erroneous control operation possibly arising, for instance, when the infusion system is transferred together with a patient receiving the infusion. Further, the infusion operation can also be stopped automatically with an alarm raised when the infusion rate happens to deviate from a predetermined allowable range for some reason or other.

BRIEF DESCRIPTION OF THE DRAWINGS

The present invention is described in further detail in the following on reference to the accompanying drawing, in which:

FIG. 6 shows a common appearance of the present invention applied to a drip infusion system;

FIG. 7(A) shows a flow rate regulation mechanism to be used in the present invention; and FIG. 7(B) shows another flow rate regulation mechanism to be used in the present invention.

DETAILED DESCRIPTION OF THE INVENTION

Figure 1:
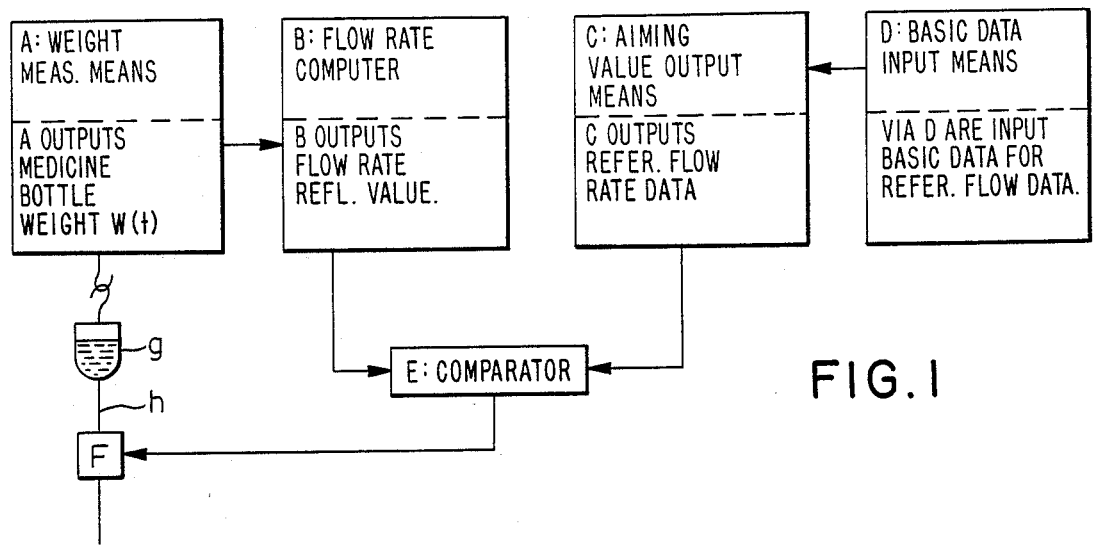
FIG. 1 is a blockdiagram showing the fundamental functional constitutionn of the present invention.

Referring to FIG. 1, which illustrates the fundamental constitution of the present invention, a weight measuring means A outputs a time-dependently varying weight W(t) of a medicine bottle g, from which a medical solution is being infused into a (not shown) patient through a infusion tube h. The varying weight W(t) is inputted to a flow rate computing means B, which computes from W(t) an existing medical solution flow rate reflecting value, for example, as an existing flow rate itself. On the other hand, a set of reference flow rate data which defines an aiming flow rate is outputted from an aiming value outputting means C. In some of the embodiments, the set of reference flow rate data consists only of an aiming flow rate itself. Any data necessary for the aiming value outputting means C to output the set of reference flow rate data are manually inputted through a basic data inputting means D. The existing flow rate reflecting value outputted from the flow rate computing means is compared, at a comparator E, with the set of reference flow rate data outputted from the aiming value outputting means C. Then the comparator C outputs a flow rate regulation signal to a flow rate regulation mechanism F interposed midway of the infusion tube h. The flow rate regulation mechanism finally controls the flow rate of the medical solution at a predetermined aiming value.

Figure 2A:
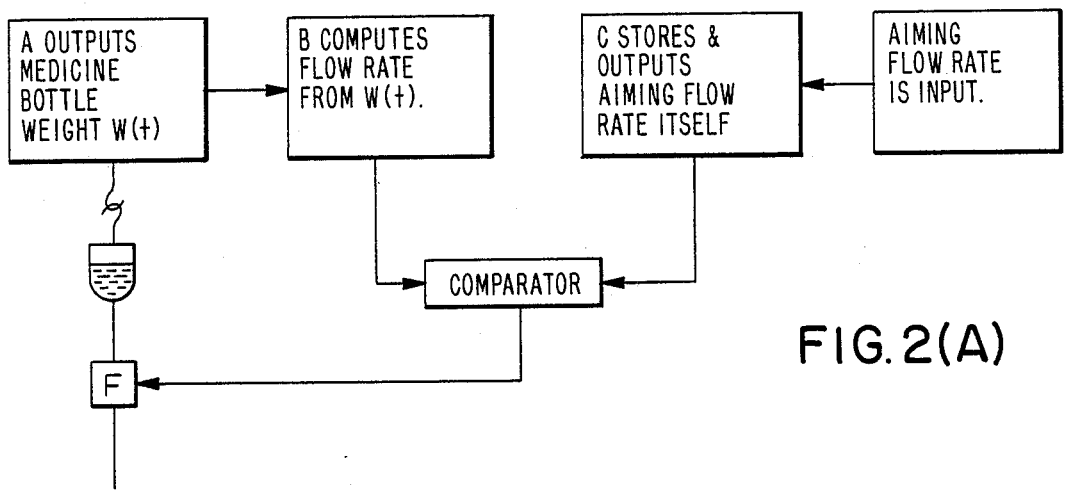
FIG. 2(A) is a blockdiagram showing the functional constitution of a first embodiment of the present invention.
Figure 2B:
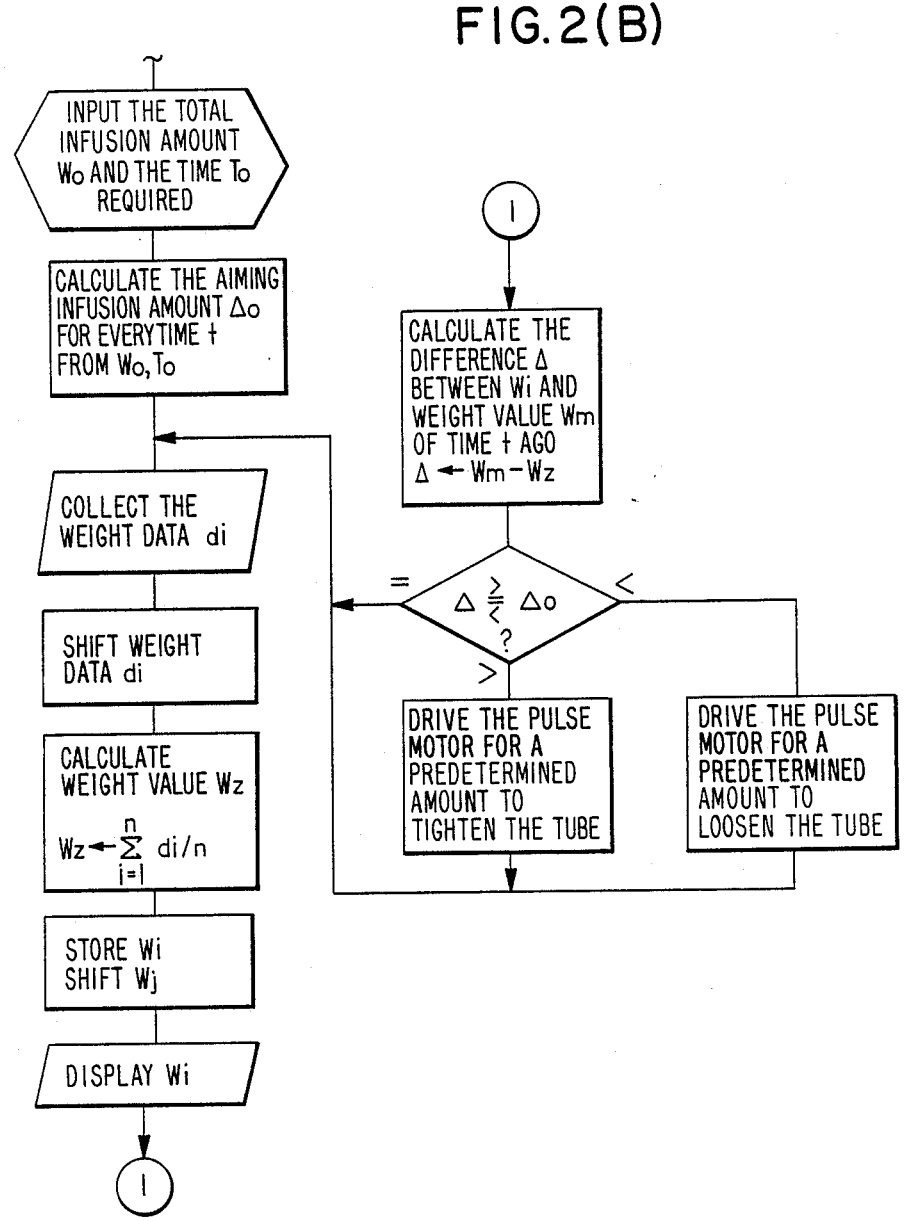
FIG. 2(B) shows a flow chart showing the operation of the above first embodiment.
Figure 5A:
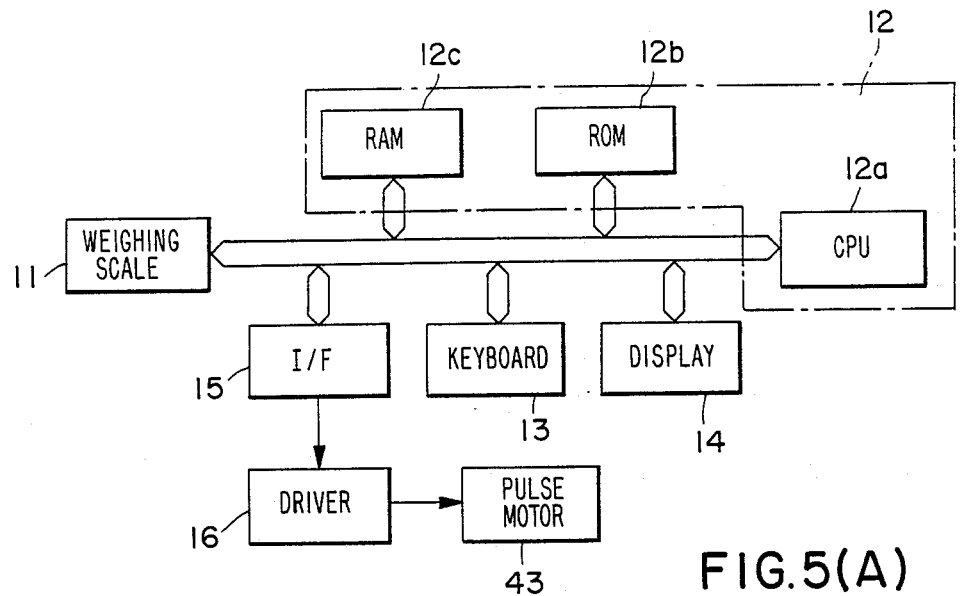
FIG. 5(A) shows a computerized electronic constitution common to the above first, second and third embodiments of the present invention.
Figure 5B:
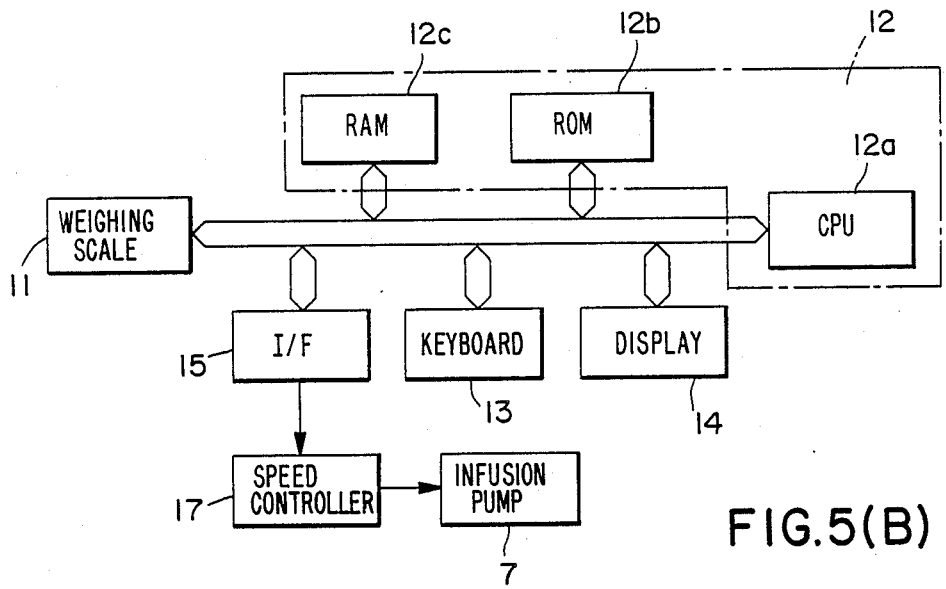
FIG. 5(B) shows a partial electronic constitution of the modifications of the above three embodiments.

In the following is described a first embodiment of the present invention. According to FIG. 2(A) diagrammatically showing the function of this first embodiment, the existing flow rate reflecting value (B) is an existing flow rate itself; the aiming value outputting means C is a simple memory, and the set of reference flow rate data outputted therefrom consists only of an aiming flow rate; and therefore, the set of basic data to be inputted through the basic data inputting means D also consists of the aiming flow rate. Such a functional constitution is practiced in an electronic system as shown in FIG. 5(A). In the figure, a weighing scale 11 for weighing a medicine bottle g (FIG. 2(A)) containing a medical solution consists, for example, of a load cell and an amplifier combined with an A-D converter. A series of time-dependently varying weight data W(ti) (ti: time) outputted from the weighing scale 11 is transferred to a microcomputerized arithmetic control part 12, which includes a CPU 12a to practice an arithmetic program and to control instruments concerned, a ROM 12b, and a RAM 12c. The RAM 12c has a first, a second and a third areas. The first area always stores n successive weight data W(ti) from the weighing scale 11 with the oldest datum shifted each time a newest weight datum is inputted. Each time the newest datum is taken in, the n weight data are subjected to an arithmetic operation of averaging. The thus obtained successive average values are transferred, as proper values Wj (j: integers) of the time-dependently varying weight of the medicine bottle g (FIG. 2(A)), to the second area, which always accepts m values of Wj (W1, W2, . . . , Wm) with the oldest value W1 shifted each time a newest value Wm+1 is taken in as W1. Further, each time the second area is thus renewed, a difference dW=W1−W2 is calculated as a value representing the average infusion flow rate in the time period To defined by (m−1) times the (constant) time interval between two adjacent calculation operations of Wj and Wj+1. Incidentally the time period To is usually selected to be several minutes. On the other hand the third area stores as an aiming infusion flow rate a weight value Wa to be infused in the same time period as To. The weight value Wa is inputted through a keyboard 14 manually in advance. The above weight difference dW representing an existing flow rate is compared with the weight value Wa representing an aiming flow rate. The result of comparison is outputted through an interface 15 to a driver 16 of a pulse motor 43, which is attached to an infusion flow rate regulation mechanism F (refer to FIG. 2(A)) devised so as to adjust the clamping degree of the infusion tube h (FIG. 2(A)). The infusion flow rate regulation mechanism F is later described in detail in conjunction with the description of an outward appearing setup of the embodiment. In the comparison of dW with Wa, if dW exceeds Wa, the driver 16 drives the pulse motor 43 to squeeze the infusion tube; if dW is smaller than Wa, the pulse motor 43 is driven to loosen the clamping of the infusion tube; and if dW is equal to Wa, the pulse motor 43 is not driven, and the degree of clamping the tube is kept unchanged. The above described operation is carried out in accordance with a program stored in the ROM 12b. The program is summarized in the form of a flow chart shown in FIG. 2(B) as a help for understanding the operation of this first embodiment.

The outward appearance of the embodiment is shown in FIG. 6, which illustates a common appearance of the present invention applied to a usual drip infusion system. A housing 1, which is mounted on top of the pole 2 of a drip infusion system, encloses therein the electronic part shown in FIG. 5(A) including the weighing scale 11 with the keyboard 13 and the display 14 made to appear on the front panel of the housing 1. The medicdine bottle g of the drip infusion system is hanged down on a hook 11a having a mechanical connection to the weighing scale 11 hidden by the housing 1. From the medicine bottle g is led the infusion tube h to a (not shown) patient through the flow rate regulation mechanism F. Midway of the infusion tube h there may be provided a drip chamber d. The detail of the flow rate regulation mechanism F is described on reference to FIG. 7(A), which shows a cross-sectional view of the mechanism. Referring to FIG. 7(A), the flow rate regulation mechanism F consists of a holder 41 having a cut-in groove 41a, an eccentric cam 42 provided in the groove 41 and the pulse motor 43 for rotating the cam 42. Between the bottom of the groove 41a and the eccentric cam 42 is inserted the infusion tube h. In such a constitution of the flow rate regulation mechanism F, the degree of throttling the infusion tube h is varied depending on the rotation angle of the eccentric cam 42. The electric wiring to the the pulse motor 43 from the driver 16 hidden by the housing 1 is not shown in FIG. 6.

A second embodiment of the present invention is described in the following on reference to FIG. 3(A), which the functional constitution of the embodiment. In this embodiment, though the part of deriving an existing flow rate and the reference flow rate data are similar to those of the first embodiment, the aiming value outputting means C consists of a memory Ca and an aiming flow rate computing means Cb. The meory Cb stores, as an aiming flow rate defining data, a total weight Wo to be infused in an aiming time period To. The aiming flow rate computing means Cb first derives a remaining weight from the weight data outputted from the weighing scale similar to that employed in the first embodiment and then computes, from the above derived remaining weight, a flow rate necessary for the remaining weight to be completely infused at the end of the aiming time period To. Such a functional constitution is practiced, similarly to the case of the first embodiment, in a computerized electronic system as shown in FIG. 5(A).

Figure 3B:
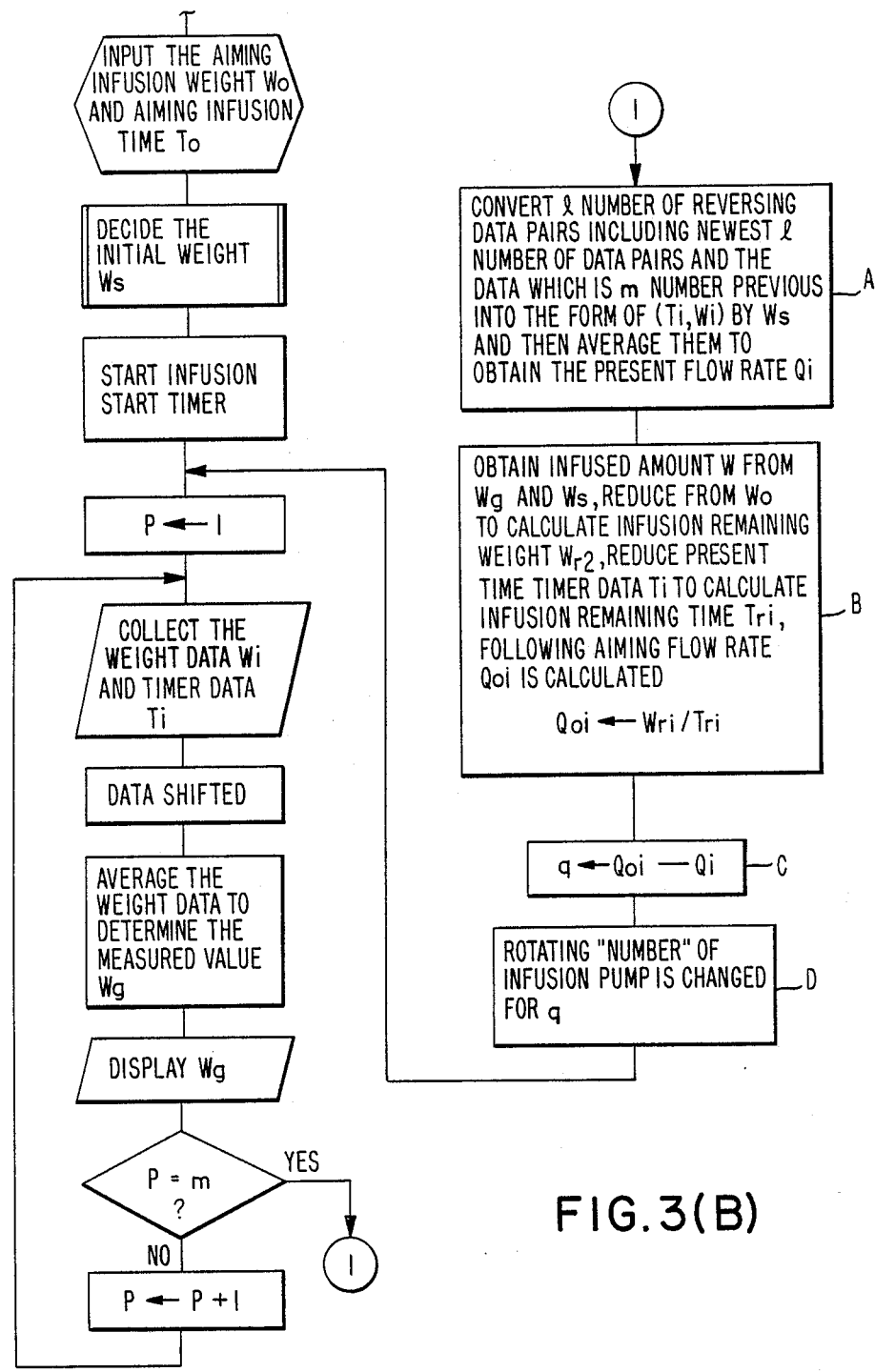
FIG. 3(B) is a flow chart showing the operation of the above second embodiment.
Figure 3A:
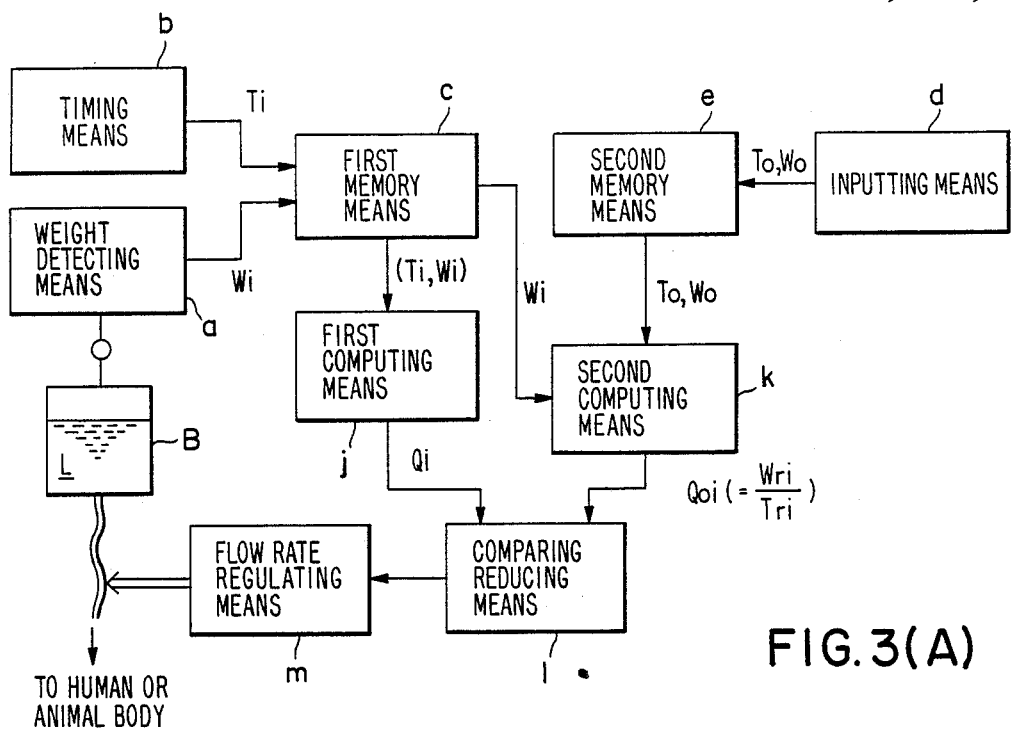
FIG. 3(A) is a blockdiagram showing the functional constition of a second embodiment of the present invention.

The program to practice the above function is shown in FIG. 3(B). The outward appearance is similar to that of the first embodiment and shown in FIG. 6.

Figure 4A:
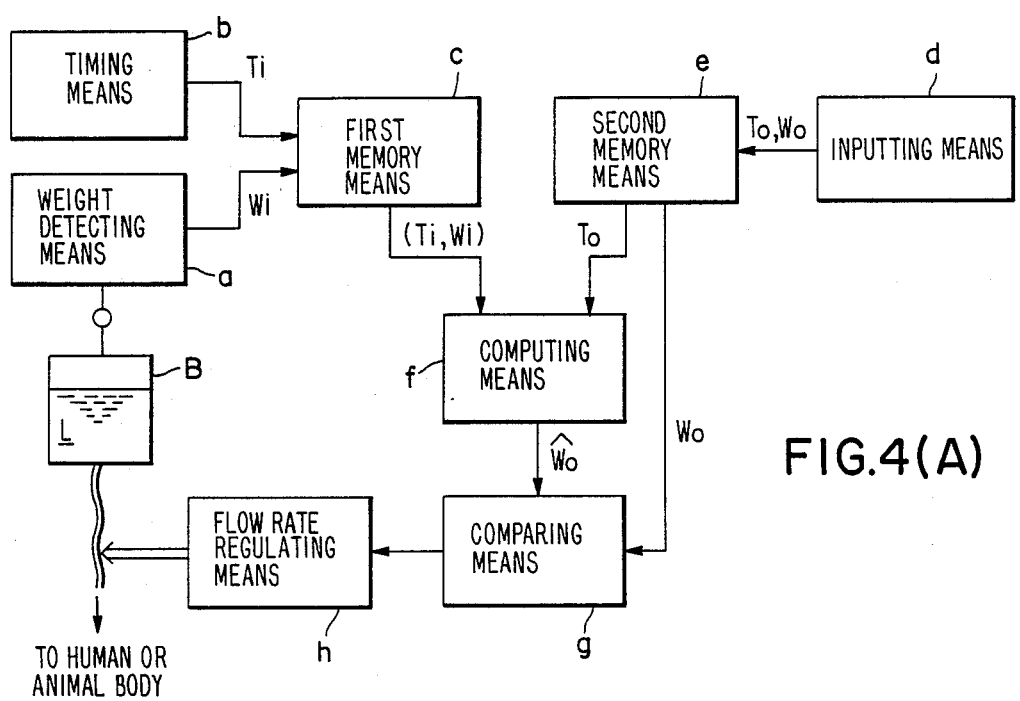
FIG. 4(A) is a blockdiagram showing the functional constitution of a third embodiment of the present invention.
Figure 4B:
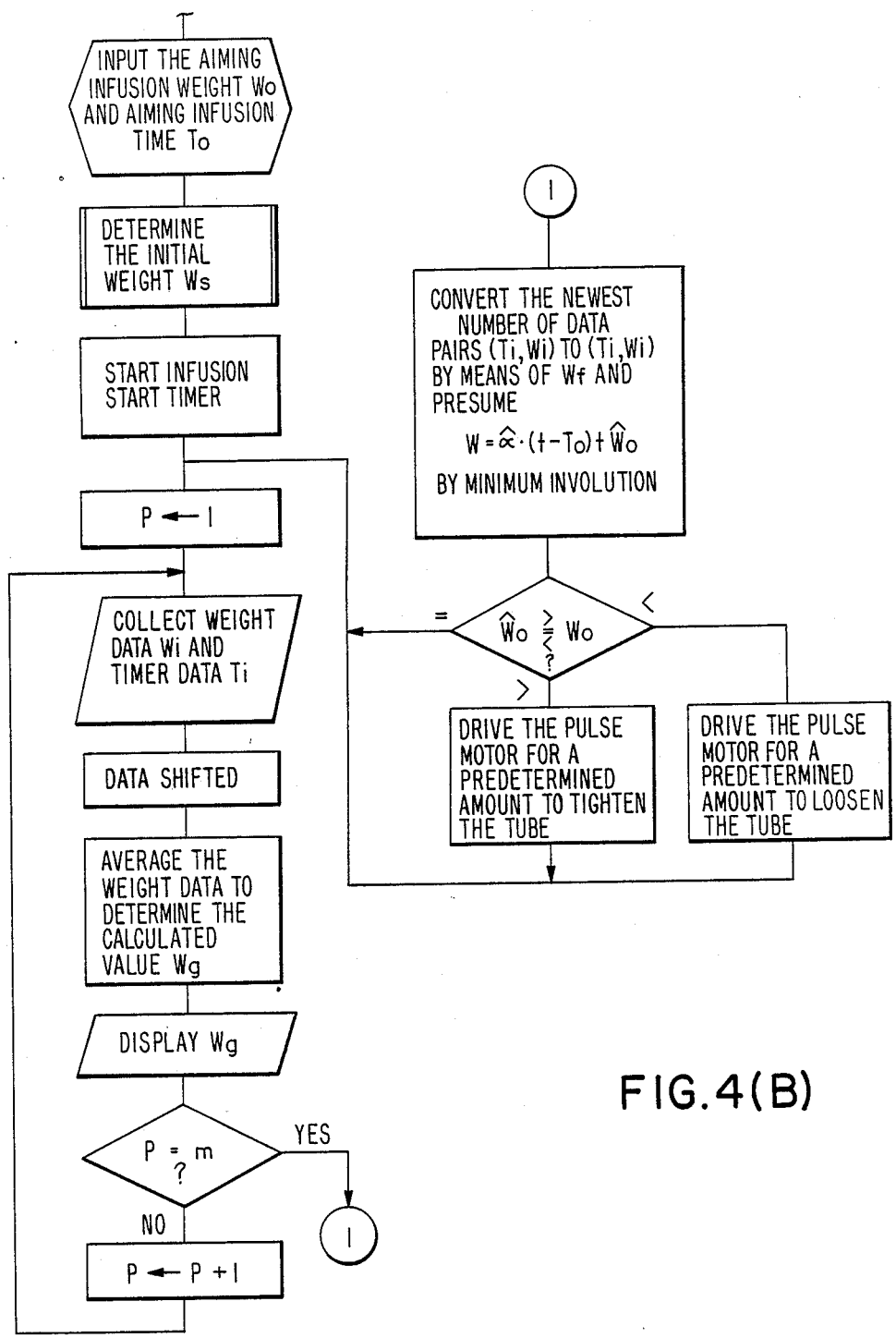
FIG. 4(B) is a flow chart showing the operation of the above third embodiment.

In the following is described a third embodiment of the present invention. In this embodiment (refer to FIG. 4(A), the existing flow rate is calculated as an estimated total weight considered to be infused at the end of an aiming time period in which an aiming total weight should be completely infused. Such a function of this embodiment is also practiced in the computerized electronic system as shown in FIG. 5(A). The program to practice the function of the embodiment is shown in the form of a flow chart in FIG. 4(B).

Further, all the above embodiment can be modified by adding an alarming means for alarming in an emergency and/or means for stopping the control operation.

We claim:

1. A drip infusion rate control apparatus for controlling the flow rate of a medical solution to be infused into a human or animal body by means of a drip infusion system, said apparatus comprising:
   a weight measuring means for measuring the weight of a medicine bottle containing a medical solution being infused into a human or animal body through an infusion tube led out from said medicine bottle;
   an existing flow rate data computing means for computing, by using at least time-dependently varying weight data outputted from said weight measuring means, an existing flow rate reflecting value which reflects an existing flow rate of said medical solution flowing in said infusion tube;
   an aiming value outputting means for outputting a set of reference flow rate data defining an aiming flow rate expected to said medical solution;
   a basic data inputting means for inputting a set of basic data necessary for said aiming value outputting means to output said set of reference flow rate data;
   a comparator for comparing said existing flow rate reflecting value with at least one of the reference flow rate data contained in said set of reference flow rate data, and outputting a flow rate control signal; and
   a flow rate regulating mechanism interposed midway of said infusion tube, said mechanism being operative according to said flow rate control signal outputted from said comparator.

2. A drip infusion rate control apparatus defined in claim 1, wherein said existing flow rate reflecting value is an existing flow rate itself of said medical solution flowing in said infusion tube; said set of basic data consists of an aiming time period and an aiming total quantity of medical solution aimed to be infused in said aiming time period; and said set of reference flow rate data consists only of a reference flow rate enabling an existing residual quantity of medical soltution to be infused completely at the end of said aiming time period; and wherein said aiming value outputting means consists of a basic data memory and a flow rate computing means, said basic data memory being for storing and outputting said aiming time period and said aiming total quantity of medical solution aimed to be infused in said aiming time period, and said flow rate computing means computing said reference flow rate from said aiming time period and said time-dependently varying weight data outputted from said weight measuring means.

3. A drip infusion rate control apparatus defined in claim 2, wherein said aiming total quantity is an aiming total weight.

4. A drip infusion rate control apparatus defined in claim 1, wherein said existing flow rate reflecting value is an estimated total infusion quantity expected at the end of an aiming time period; said set of basic data consists of said aiming time and an aiming total quantity of medical solution aimed to be infused in said aiming time period; and said set of reference flow rate data consists only of said aiming total quantity of medical solution aimed to be infused in said aiming time period, and wherein said existing flow rate data computing means computes, using said aiming time period and said time-dependently varying weight data outputted from said weight measuring means, said estimated total infusion quantity; said aiming value outputting means is a basic data memory for storing and outputting said aiming time period and said aiming total quantity of medical solution aimed to be infused in said aiming 5. A drip infusion rate control apparatus defined in claim 4, wherein said estimated total infusion quantity is an estimated total infusion weight expected at the end of said aiming time period; and said aiming total quantity is an aiming total weight of medical solution aimed to be infused in said aiming time period.

6. A drip infusion rate control apparatus defined in any one of claim 1 and 2 to 5, wherein said flow rate data computing means is devised so that said existing flow rate reflecting value may be kept constant through a manual switchin operation for the purpose of keeping the infusion rate of said medical solution constant.

7. A drip infusion rate control apparatus defined in any one of claim 1 and 2 to 5, wherein an infusion stopping means is provided, said means being devised so as to rais an alarm and stop the infusion when the flow rate of said medical solution flowing in said infusion tube deviates from a predetermined allowable range.

8. A drip infusion rate control apparatus for controlling the flow rate of a medical solution to be infused into a human or animal body by means of a drip infusion system, said apparatus comprising:
   a weight measuring means for repetitively measuring the weight of a medicine bottle containing a medical solution being infused into said human or animal body through an infusion tube led out from said medicine bottle at predetermined time increments;
   an existing flow rate data computing means for computing, by using at least time-dependently varying weight data outputted from said weight measuring means, an existing flow rate reflecting value which reflects an existing flow rate of said medical solution flowing in said infusion tube;
   a basic data inputting means for inputting a set of basic data necessary for an aiming value, said basic data comprising a total weight to be infused and a total time for infusion;
   an aiming value outputting means for computing and outputting a set of reference flow rate data defining an aiming flow rate for said medical solution based upon said timedependently varying weight data, total weight to be infused and an amount of time remaining of said total time;
   a comparator for comparing said existing flow rate reflecting value with at least one of the reference flow rate data contained in said set of reference flow rate data, and outputting a flow rate control signal; and
   a flow rate regulating mechanism interposed midway of said infusion tube, said mechanism being operative according to said flow rate control signal output from said comparator;
   whereby said flow rate is repetitively adjusted such that said total amount to be infused in infused in said total time.

* * * * *